United States Patent [19]

Fountain

[11] 4,295,360
[45] Oct. 20, 1981

[54] TENSION MEASURING APPARATUS

[75] Inventor: Frank S. Fountain, Wilmington, Del.

[73] Assignee: E. I. Du Pont de Nemours and Company, Wilmington, Del.

[21] Appl. No.: 111,665

[22] Filed: Jan. 14, 1980

[51] Int. Cl.³ .................... G01N 25/00; G01N 33/36
[52] U.S. Cl. ...................................... 73/15.6; 73/160; 73/862.48
[58] Field of Search ........................................ 73/144

[56] References Cited

U.S. PATENT DOCUMENTS 3,354,711 11/1967 Seney .
3,512,406 5/1970 Roberts .................................. 73/144
3,554,025 1/1971 Andersson et al. .................... 73/144
3,777,959 12/1973 Seney .
4,052,891 10/1977 Bartlett ................................. 73/144
4,067,234 1/1978 Seney .

OTHER PUBLICATIONS

Annon, Research Disclosure #15046, Oct. 1976.

Primary Examiner—S. Clement Swisher

[57] ABSTRACT

A single-pin guide tensiometer fitted with strain-detecting element that is flattened to respond only in a direction perpendicular to the flat faces of the elements. Moreover by rotating the tensiometer 90 degrees, threadline tension in the opposite direction is measured.

2 Claims, 5 Drawing Figures

TENSION MEASURING APPARATUS

BACKGROUND OF THE INVENTION

This invention relates to measurement of tension in a moving threadline, and more particularly to a single pin guide tensiometer.

Disclosure No. 15046, entitled "Method for Determining Bulk and Dyeability of Draw Textured Yarn" and published in the October 1976 issue of Research Disclosure, describes a testing apparatus for measuring yarn tension during drawing of a drawtexturing feed yarn. It documents that it is known that drawtension correlates empirically with yarn properties of drawtextured yarn. The apparatus described is designed to measure only drawtension and to do so only at a single preselected draw-ratio as determined by the ratio of yarn-forwarding speeds of its draw and feed rolls. Moreover, the tensiometer suggested for use (a Rothschild tensiometer) is one which (1) employs yarn guides in addition to the strain-detecting guide, thereby causing undetermined frictional forces to be included in the detected tension, and (2) is oriented such that components of both upstream and downstream yarn tensions are included in the detected tension.

There also exists a commercially available drawtension instrument known as the "Dynafil" (manufactured by Textronico). It uses stepped-driven rolls along with separator guides for both feed and draw rolls. Multiple yarn wraps on each roll system make stringup laborious and not susceptible to automated serial handling of successive samples. Moreover, its tension detector is a rather complicated lever arrangement in which the yarn under test wraps 180 degrees about a guide, thus measuring the sum of upstream and downstream tensions and providing no means for compensating for frictional forces at the guide. A variety of interchangeable rolls is provided to enable selection of a range of draw ratios. Each such change in draw ratio, however, necessitates another tedious stringup of the yarn.

SUMMARY OF THE INVENTION

The present invention is embodied in a testing device which overcomes the disadvantages of known devices. It is capable of completely automatic operation. Besides its capability of measuring drawtension at preselected yarn speed and draw ratio, it is capable of continuous variation in both yarn speed and draw ratio, thus rendering it a dynamic stress-strain analyzer for use in place of static stress-strain analyzers commonly employed. Moreover, by simple rotation of its strain-sensing yarn guide, it measures either upstream or downstream yarn tension without including uncompensated frictional forces or tension components other than that selected for measurement. It, therefore, provides for measuring yarn frictional coefficients, too, which are useful, for example, in correlation of the effects of different yarn finishes.

These advantages are provided in a tension-testing device which includes, in series along the threadline:

A. feed-roll means driven directly by a first electric motor with associated electronics for establishing and maintaining a preselected but continuously variable first yarn speed, B. a nonrotating guide means of circular cross-section positioned to change yarn direction by a fixed angle, $\alpha$, C. a yarn heater of the radiant type free of contact with the travelling yarn, D. draw-roll means driven by a second electric motor with associated electronics for establishing and maintaining a preselected but continuously variable second yarn speed, and is particularly characterized in that (1) guide means (B) is mounted at the end of a coaxial shaft including strain-sensing elements, (2) strain-sensing elements include a portion of the coaxial shaft of reduced cross-sectional size being rectangular in cross-section, having flat faces several times wider than the thickness, and having strain gages affixed to its flat faces near the fixed end of the portion of reduced cross-section.

(3) the strain gages vary in some electrical property (e.g., resistance) in proportion to the strain produced along the portion of reduced cross-section, and (4) guide-means (B), together with its coaxial shaft, is adjustable to two angular positions wherein the flat faces of the portion of reduced cross-section are parallel to either the upstream or the downstream threadlines.

A further preferred embodiment is disclosed for automatic stringup of a yarn to be tested. It includes means to open feed-roll means (A) and draw-roll means (D) during stringup, a first air-jet means along the threadline near a yarn-supply for propelling the yarn end through the open feed-roll means (A) to beyond guide means (B), a yarn deflector associated with guide means (B) for directing the yarn end toward the entrance of yarn heater (C), and a second air-jet means along the threadline positioned to propel the yarn end through the yarn heater (C) and the open draw-roll means (D). Preferably a third air-jet forwarding means is positioned to direct the strung-up yarn end to waste and a threadline sensor is positioned on the threadline between the draw-roll means (D) and the third air-jet forwarding means. Still further, a yarn cutter actuable to terminate a test is preferably positioned along the threadline adjacent to the first air-jet means.

The device may include a computer for controlling stringup, the establishment and control of roll-speeds, tension testing, selection of the angular orientation of guide means (B), sequence of events, and computation and print-out of experimental results.

DETAILED DESCRIPTION OF THE ILLUSTRATED EMBODIMENT

Figure 1:
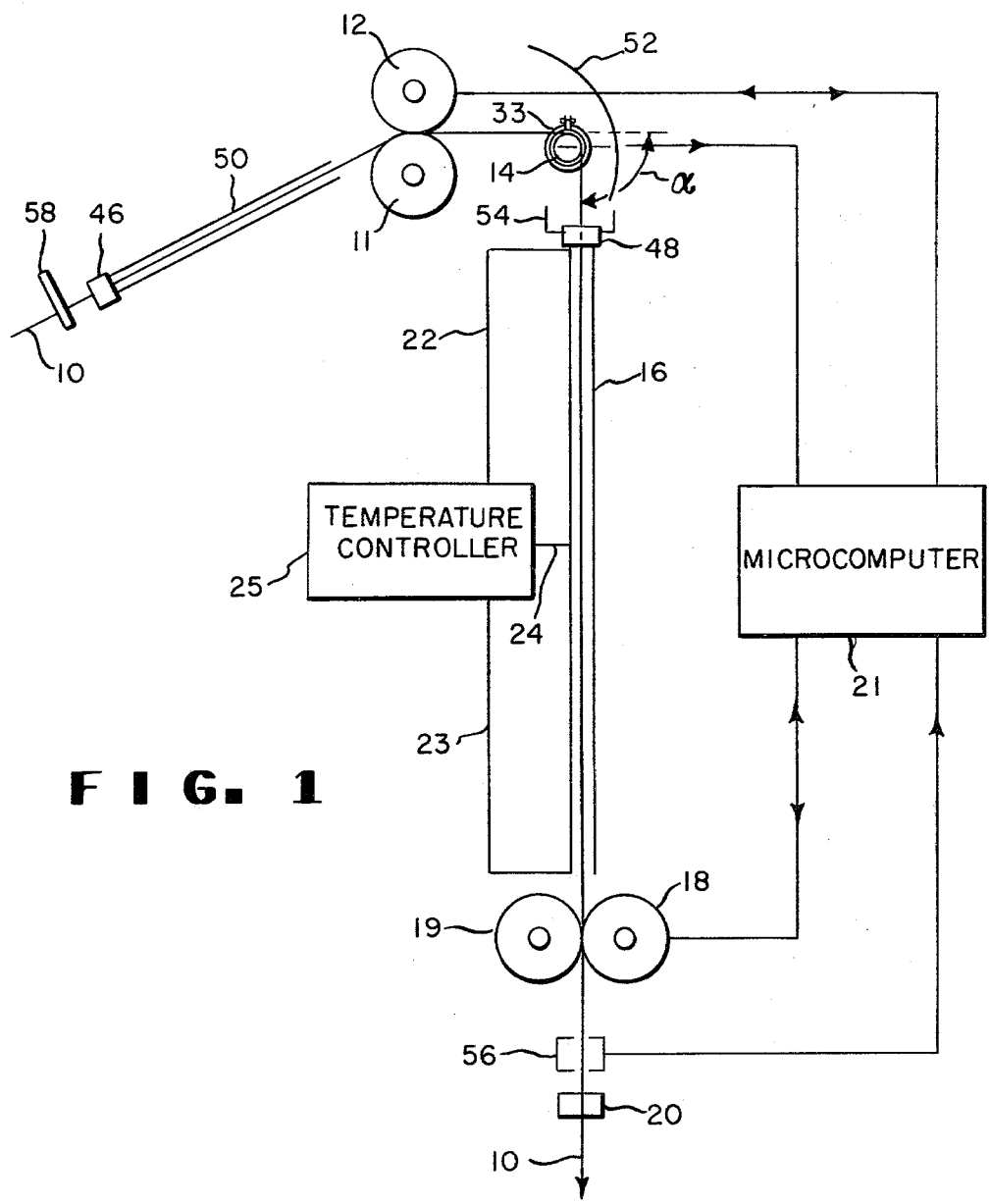
FIG. 1 is a schematic representation of the overall apparatus.

With reference to FIG. 1, a typical embodiment of the invention is described in its operating configuration. Threadline 10 proceeds between feed-rolls 11, 12, around guide means 14, through tubular yarn heater 16, through draw-rolls 18, 19, and to waste via air-jet 20.

Feed-roll 12 is hard-surfaced and smooth and is driven by a coaxial synchronous electric motor (not shown) capable of continuously variable speeds. Roll 11 is a soft-surfaced follower roll which can be moved away from driven roll 12 to open the gap between them. Because the soft surface of follower roll 11 is subject to relatively rapid wear, means (not shown) are preferably provided to cause it to slowly move along its axis during operation so as to distribute the wear. To facilitate stringup of yarn, one of rolls 11, 12 is preferably capable of being moved away from the other temporarily so as to open a gap between them.

Figures 4A, 4B:
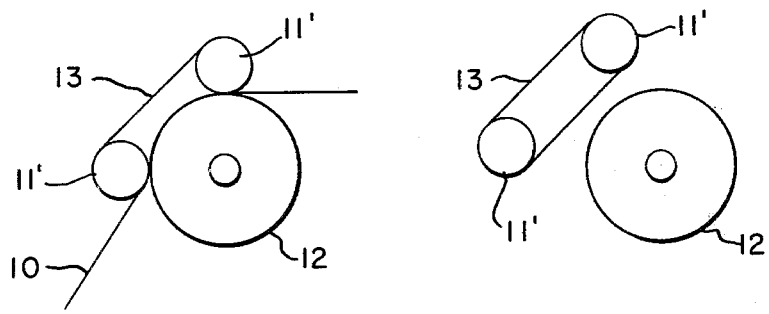
FIGS. 4a and 4b show Casablanca rolls in closed (a) and opened (b) configurations.

Draw-roll 18 and its follower roll are structured and operated exactly as described above for feed-roll means 11, 12. Both may alternatively be Casablanca rolls as depicted in closed (a) and opened (b) states in FIGS. 4a and 4b. The driven roll 12 is axially fixed. The follower assembly comprises 2 rolls 11' about which is passed a belt 13. In the opened state (4b), the follower assembly is moved away from roll 12. In the closed state (4a), the assembly is urged against the surface of roll 12 to grip travelling yarn 10 along the arc of contact of belt 13 with the surface of roll 12.

Heater 16 is of the radiant type, free of any contact with yarn 10. It should be as long as is practical within the size limitations of a testing instrument, lengths of the order of one meter generally sufficing. In a preferred version, heater 16 is a stainless steel tube between the ends of which a low voltage is applied via electrical leads 22, 23 from temperature controller 25. Any of numerous commercially available temperature controllers may be used together with a temperature sensing probe as indicated by lead 24. Because air is preferably passed through heater 16 during stringup, and because rapid temperature changes may be desired during a test, it is preferred that the heating system be designed to provide rapid recovery times.

Figure 2:
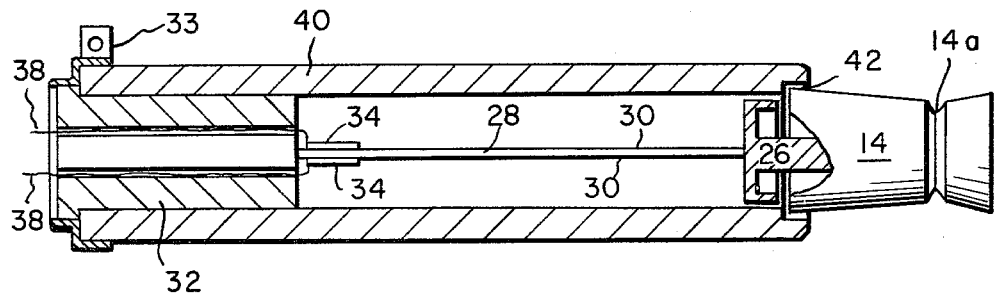
FIGS. 2 and 3 are schematic representations in partial cross-section of guide means (B) and its associated strain-sensing elements.
Figure 3:
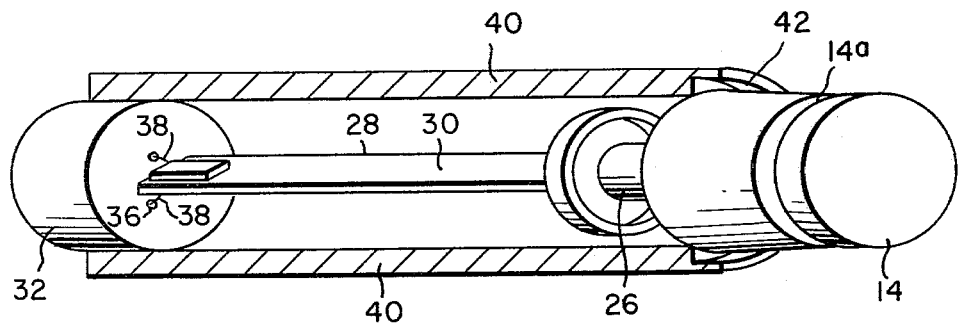

In passing from feed rolls 11, 12 to heater 16, yarn 10 changes direction by an angle $\alpha$ about guide 14. Preferably $\alpha$ is 90 degrees, but it may be less (or more) to fit space limitations. FIG. 2 shows in schematic detail the guide 14 together with its assembly containing the strain-sensing elements. Groove 14a contains the yarn while it changes direction. Guide 14 is rigidly attached to mounting element 26 which is integral with a shaft 28 of reduced, rectangular cross-section providing for flexure in response to forces generated during change of yarn direction about guide 14. FIG. 2 shows the narrow edge of shaft 28, the other rectangular dimension (perpendicular to the plane shown) being several (e.g., 5 to 10) times greater to provide relatively wide, parallel, and flat faces 30. The other end of shaft 28 is integral with massive mounting plug 32 which is shown fitted in a fixed clamp 33. Clamp 33 can be released then retightened after limited rotation of guide 14. Adhered to faces 30 adjacent to plug 32 are strain gages 34 which, in a preferred embodiment, are formed of semiconductor elements or wire-type strain gages according to well-established engineering practice. The type of strain gage employed is not critical and may be any of the well-known wire, foil, or semi-conductor-crystal types. It must, however, provide a change in an electrical property (e.g., resistance) which is proportional to flexure of shaft 28. Holes 36 are provided for passage of electrical leads 38 through plug 32. A cylindrical protective sheath 40 is fitted to plug 32 and extends to surround a little of the base of guide 14 where a gap 42 is machined to prevent excessive flexure of shaft 28 in the event of tension surges.

It is apparent from the above description that the assembly of FIG. 2 is designed to detect strains only perpendicular to flat faces 30 of shaft 28. Aside from this requirement, structure of the assembly is not critical to operation. In FIG. 1, guide 14 is shown with an internal line representing the orientation of the flat faces 30, i.e., parallel to the approaching (upstream) threadline 10. In this arrangement, the upstream yarn tension ($T_1$) has no component perpendicular to faces 30 and therefore contributes nothing to flexure of shaft 28. All measured tension results from the downstream tension ($T_2$) and equals $T_2 \sin \alpha$. Likewise, when the assembly of FIG. 2 is rotationally adjusted so faces 30 are parallel to the downstream threadline, the measured tension is $T_1 \sin \alpha$. If $\alpha$ is 90 degrees, the sine terms are both unity. Thus, by rotational adjustment of the assembly of FIG. 2, $T_1$ and $T_2$ are individually measured. From them, frictional coefficient $\mu$ is easily computed from the well-known formula $$T_2/T_1 = e^{\mu\alpha} (\alpha \text{ in radians}).$$

Preferably the whole sequence of operations is interfaced for computer control, especially microcomputer control as depicted in FIG. 1 by element number 21. Particularly well suited are the Hewlitt-Packard 9800 series desktop computers, especially HP 9825 or HP 9835B together with an HP 6940B multiprogrammer. This system uses a multichannel interface system for which interface "cards" are provided to enable handling directly a broad variety of digital or analog inputs. Speed control is especially simplified if the electric motor drives for rolls 12 and 18 (FIG. 1) are digitally controlled servomotors with speed proportional to applied voltage. Synchronous motors are also suitable. Temperature control is subject to computerized handling, but, in the embodiment shown, is handled by a separate control system.

For fully automatic stringup, forwarding air-jets 46 and 48 are provided. Air-jet 46 preferably has a cylindrical tail 50 extending almost to feed-roll 12 for guiding thread 10, and air-jet 48 is mounted at the entrance end of heater 16.

In operation, roll systems 11, 12 and 18, 19 are first opened. The end of a yarn supply is brought close to air-jet 46, and all air-jets (46, 48, and 20) are turned on. The yarn 10 is propelled between rolls 11, 12 over and beyond guide 14 to impinge on a deflector 52 which directs the advancing end downward into cup 54 surrounding air-jet 48. Air-jet 48 propels the yarn through heater 16 and through opened rolls 18, 19 to air-jet 20 where the yarn 10 is transported to waste. A yarn detector 56 (any of numerous available devices) provides a "completed stringup" signal to the microcomputer 21 which then closes the roll systems 11, 12 and 18, 19 and turns off air-jets 46 and 48. After a signal is provided that set-point temperature has been reached, the microcomputer begins a preprogrammed sequence of roll-speed, draw-ratio, and guide 14 orientations together with appropriate printout of desired yarn speeds, tensions, frictional coefficients, and other tensile parameters computed therefrom. At the end of the preprogrammed sequence of events, the test is terminated by activating yarn cutter 58, opening roll systems 11, 12 and 18, 19, and indexing another yarn sample opposite air-jet 46. It is, of course, also practical to index sequential yarn samples under computer control by providing detectors near air-jet 46 to signal that a new sample is in place for testing.

The tension testing device of this invention for the first time provides for individual discrimination between upstream and downstream yarn tensions with no component of one in any way affecting the measurement of the other. Thus, the additional computation of frictional coefficients is enabled. Because roll speeds are continuously variable, any speed and/or draw ratio may be established without any restringing of the apparatus. Further, draw rolls may be operated more slowly than feed rolls for the measurement of shrinkage tensions. This dynamic system is, in fact, so versatile and rapid in operation that it can completely substitute for static stress/strain analyzers commonly used in testing laboratories to measure tenacities, elongations, moduli, and other derived tensile properties of yarns.

I claim:

1. In an apparatus for measuring yarn tension while the yarn is being drawn that includes means for feeding the yarn from a source through a heater to a drawing means, a yarn direction-changing tension-measuring device located between the feed means and the heater comprising: a shaft having a plug attached to one end and a direction-changing guide mounted at its other end around which yarn passes, said shaft being of rectangular cross section with wide flat surfaces several times greater than its narrower surfaces to allow for flexure in response to forces generated during change of yarn direction about said guide, a strain transducer connected to opposite wide flat surfaces of said shaft and means for mounting said plug for limited rotation to detect only forces perpendicular to said wide flat surfaces.

2. The apparatus as defined in claim 1, including means attached to said plug and extending to the other end of the shaft and surrounding a portion of said guide for limiting flexure of said shaft in the event of tension surges.

* * * * *